US012558073B2

(12) United States Patent
Wada et al.

(10) Patent No.: US 12,558,073 B2
(45) Date of Patent: Feb. 24, 2026

(54) ULTRASOUND PHANTOM AND METHOD FOR MANUFACTURING ULTRASOUND PHANTOM

(71) Applicant: CANON KABUSHIKI KAISHA, Tokyo (JP)

(72) Inventors: Kyohei Wada, Tokyo (JP); Chiaki Nishiura, Tokyo (JP); Ryo Ogawa, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 684 days.

(21) Appl. No.: 17/931,218

(22) Filed: Sep. 12, 2022

(65) Prior Publication Data

US 2023/0097162 A1    Mar. 30, 2023

(30) Foreign Application Priority Data

Sep. 30, 2021    (JP) ................................. 2021-161704

(51) Int. Cl.
*A61B 8/00*        (2006.01)
(52) U.S. Cl.
CPC .................................... *A61B 8/587* (2013.01)
(58) Field of Classification Search
CPC ................................ A61B 8/587; A61B 8/546
See application file for complete search history.

(56) References Cited

U.S. PATENT DOCUMENTS 5,502,181 A      3/1996  Kojima et al.
5,625,137 A  *  4/1997  Madsen ................. A61B 8/587
                                                            73/1.84

9,597,058 B2      3/2017  Kanayama et al.
10,231,710 B2    3/2019  Kanayama
2011/0067624 A1 *  3/2011  Cain ..................... G09B 23/286
                                                            116/203
2012/0227478 A1 *  9/2012  Mukai ..................... G02B 21/34
                                                            73/118.01
2014/0260524 A1 *  9/2014  Seo ......................... G01N 29/30
                                                            252/583

FOREIGN PATENT DOCUMENTS

JP          5-317008 A        12/1993
JP          2015-054056 A      3/2015
JP          5787286 B2          9/2015
KR          20100129263 A  *  12/2010    ............. A61P 27/02
WO          2009/010898 A2      1/2009

* cited by examiner

*Primary Examiner* — Francis C Gray
(74) *Attorney, Agent, or Firm* — Venable LLP

(57)            ABSTRACT

An ultrasound phantom comprising: water; agar; a thickening polysaccharide; and a water-retention auxiliary agent, wherein when a first phase transition point is defined as a temperature at which an aqueous dispersion liquid of the agar is solated by temperature raising and becomes a solated aqueous solution of the agar, and a second phase transition point is defined as a temperature at which the solated aqueous solution of the agar is gelated by temperature lowering, the thickening polysaccharide does not have a phase transition point at which an aqueous solution of the thickening polysaccharide is gelated by temperature lowering in a temperature range from the second phase transition point to the first phase transition point, and a polar term $\delta P$ of Hansen solubility parameters of the water-retention auxiliary agent is 13.0 $MPa^{0.5}$ or more.

14 Claims, No Drawings

ULTRASOUND PHANTOM AND METHOD FOR MANUFACTURING ULTRASOUND PHANTOM

BACKGROUND OF THE INVENTION

Field of the Invention

The present disclosure relates to an ultrasound phantom and a method for manufacturing an ultrasound phantom.

Description of the Related Art

A biological tissue-mimicking phantom that simulates body tissues is used for calibration of and implementation of functions in medical diagnostic apparatuses such as an acoustic wave (for example, ultrasound) diagnostic apparatus, a magnetic resonance imaging (MRI) diagnostic apparatus, a computed tomography (CT) apparatus, an X-ray diagnostic apparatus, and a near-infrared imaging (NIRI) apparatus. These apparatuses utilize electromagnetic waves such as ultrasound, X-rays, and light to monitor physical phenomena such as scattering, refraction, reflection, absorption, diffraction, and interference thereof, thereby performing diagnosis of a patient's disease.

In recent years, an ultrasound diagnostic apparatus in which the function of quantitatively evaluating the hardness (elastic modulus) of an organ by a shear wave elastography method (SWE method) is implemented is known. This is a method of observing the propagating velocity of shear waves generated by ultrasound to calculate a Young's modulus in an organ, which enables quantitative evaluation of the hardness.

Japanese Patent Application Publication No. 2015-054056 discloses an elastography apparatus that makes it easier for an operator to visually recognize an influence of shear waves, which have the property of being reflected at the interface between tissues having different hardness, by superimposing positions on a biological body to which burst waves are transmitted on an ultrasound image, thereby improving the image quality of elastic modulus images.

An ultrasound phantom is used to calibrate an elastography apparatus for calculating the hardness and hardness distribution of tissues of a biological body. It is known that favorable ultrasound characteristics can be obtained by an ultrasound phantom using a hydrogel containing agar. The ultrasound phantom using a hydrogel may be referred to as a hydrogel phantom or an agar phantom.

WO 2009/010898 discloses a hydrogel phantom in which a hydrogel containing mixed agarose, which is known as a main component of agar, is adopted as a layer simulating tissues of a biological body. WO 2009/010898 further discloses that the damping characteristics of acoustic waves are adjusted by incorporating an aluminum oxide powder in which particle diameters are different and silicon carbide in the hydrogel phantom to simulate a fat layer.

SUMMARY OF THE INVENTION

However, when applying the agar-based hydrogel as disclosed in WO 2009/010898 to the calibration of an elastography apparatus, improvement was desired in some cases from the viewpoint of reproducibility and stability over time. When a phantom produced with agar was repeatedly used as an elastic phantom, the elastic modulus and acoustic propagation characteristics were irreversibly changed in some cases. Because the calibration of an elastography apparatus is performed irregularly, an agar phantom with guaranteed reproducibility and stability over time has been desired. The reproducibility and stability over time desired for such an ultrasound phantom include reproducibility and stability over time in acoustic waves propagation characteristics.

The present disclosure provides an ultrasound phantom with guaranteed reproducibility and stability over time even when it is used repeatedly over time, and a method for manufacturing the same.

The present disclosure relates to an ultrasound phantom comprising:

water;

agar;

a thickening polysaccharide; and a water-retention auxiliary agent, wherein when a first phase transition point is defined as a temperature at which an aqueous dispersion liquid of the agar is solated by temperature raising and becomes a solated aqueous solution of the agar, and a second phase transition point is defined as a temperature at which the solated aqueous solution of the agar is gelated by temperature lowering, the thickening polysaccharide does not have a phase transition point at which an aqueous solution of the thickening polysaccharide is gelated by temperature lowering in a temperature range from the second phase transition point to the first phase transition point, and a polar term $\delta P$ of Hansen solubility parameters of the water-retention auxiliary agent is 13.0 $MPa^{0.5}$ or more.

According to the present disclosure, an ultrasound phantom with guaranteed reproducibility and stability over time even when it is used repeatedly over time, and a method for manufacturing the same can be provided.

Further features of the present invention will become apparent from the following description of exemplary embodiments.

DESCRIPTION OF THE EMBODIMENTS

In the present disclosure, the terms "from XX to YY" and "XX to YY", which indicate numerical ranges, mean numerical ranges that include the lower limits and upper limits that are the end points of the ranges. In cases where numerical ranges are indicated incrementally, upper limits and lower limits of the numerical ranges can be arbitrarily combined.

Agar (A)

Agar is a mucilage extracted from red algae such as Gracilaria and Gelidium, and is a polysaccharide consisting of at least agarose and agaropectin. Any can be used regardless of the production area, origin, and the like thereof. As the agar, so-called low-strength agar (disclosed in Japanese Patent Application Publication No. H05-317008, for example) in which molecules have been cleaved by acid treatment may be used to adjust the strength of a gel. It is preferable to use powdered agar.

The agar has a first phase transition point at which an aqueous dispersion liquid of the agar is solated by temperature raising, and a second phase transition point at which the solated aqueous solution of the agar is gelated by temperature lowering. The aqueous dispersion liquid of the agar is obtained by dispersing the agar in water. In addition, the first phase transition point is the temperature at which the aqueous dispersion liquid is solated when raising the temperature of the aqueous dispersion liquid of the agar. Furthermore, the second phase transition point is the temperature at which the solated aqueous solution of the agar is gelated when lowering the temperature thereof.

The first phase transition point is preferably a temperature at which the aqueous dispersion liquid in which the agar has been dissolved in water is solated when raising the temperature of the aqueous dispersion liquid in which 1.0% by mass of the agar has been dispersed in water from room temperature (25° C.). Furthermore, the second phase transition point is preferably a temperature at which the aqueous solution is gelated when leaving the solated aqueous solution of the agar at room temperature to lower the temperature. Generally, the first phase transition point is present at from 85° C. to 99° C., and the second phase transition point is present at from 30° C. to 45° C. In the specification of the present application, an equilibrium state in which a specific component has been "dissolved" in water to form an aqueous solution, and an equilibrium state in which a specific component has been "dispersed" in water to form a dispersion liquid are distinguished.

In the present disclosure, a gel refers to a solid state, and a sol indicates the state of having flowability. Viscoelasticity measurements can be used to determine a gel and a sol. Specifically, it can be determined by the following procedure using a dynamic viscoelasticity measurement device. Furthermore, the dynamic viscoelasticity measurement device has a shear mode in which stress is applied in the horizontal direction, and a compression and tension mode in which stress is applied in the vertical direction, but the shear mode is adopted. The value of tan δ, which is the ratio between the storage elastic modulus and the loss elastic modulus, can be calculated to determine that there is a gel when the value is 1.0 or less, and that there is a sol when the value is larger than 1.0. For the measurement frequency at this time, 0.5 Hz or 1 Hz can be adopted in consideration of the followability between the gel and a measurement jig. It is desirable that the strain at the time of measurement be from 0.01% to 0.1%. When the strain is less than 0.01%, because the gel cannot be moved sufficiently, the reliability of the measurement value cannot be obtained. Furthermore, when the strain is larger than 0.1%, because the measurement jig slips, the reliability of the measurement value deteriorates. Examples of the viscoelasticity measurement device that can be used include an MCR 302 sold by Anton Paar Japan K.K.

Agar is a hydrogel material that generally dissolves in water when being heated to 85° C. or higher in water to become a sol, and changes its structure to a gel when being cooled to 45° C. or lower. In the sol state, the entanglement of the polymer chains contained in the agar is disentangled, and it liquefies when dissolved in water. Meanwhile, at the time of cooling, the polymer chains in the agar form a double helix structure, and as the cooling progresses, higher-order entanglements are formed, resulting in gelation. From the above gelation mechanism, the Young's modulus of an ultrasound phantom correlates with the concentration of agar, which makes it possible to adjust from a soft gel to a hard gel. The ultrasound phantom is required to simulate various organs, and the range of a required Young's modulus is wide. The agar can be suitably used for adjusting this Young's modulus.

In the ultrasound phantom, at least a part of water is preferably hydrated with the agar, and the agar is preferably gelated. Furthermore, in the ultrasound phantom, the agar preferably forms a hydrogel with at least a part of water. That is, the ultrasound phantom is preferably in the form of a hydrogel. The water content of the ultrasound phantom is preferably from 50.00% by mass to 99.50% by mass, more preferably from 70.00% by mass to 99.00% by mass, further preferably from 80.00% by mass to 98.00% by mass, and further more preferably from 80.00% by mass to 95.00% by mass, for example. The ultrasound phantom may contain a thickening polysaccharide, a water-retention auxiliary agent, and the like in the hydrogel formed by water and the agar.

When the total mass of the water and the water-retention auxiliary agent is 100.00 parts by mass, the formulation amount or content of the agar is preferably from 0.25 parts by mass to 20.00 parts by mass, and it is preferably from 0.50 parts by mass to 10.00 parts by mass to obtain a uniform phantom in which there are no bubbles and the like. It is more preferably from 1.00 parts by mass to 10.00 parts by mass, further preferably from 1.25 parts by mass to 10.00 parts by mass, and further more preferably from 1.50 parts by mass to 10.00 parts by mass.

By adjusting within the above-mentioned range, an ultrasound phantom having various Young's modulus can be produced. When the formulation amount or content of the agar is 0.25 parts by mass or more, gelation easily occurs at the time of cooling. Meanwhile, when the formulation amount or content of the agar is 10.00 parts by mass or less, the viscosity of the agar heat-melted is appropriate, which makes it easy to obtain a more uniform ultrasound phantom.

Thickening Polysaccharide (B)

The ultrasound phantom contains thickening polysaccharide (B) different from the agar (A). The thickening polysaccharide does not have a phase transition point at which an aqueous solution of the thickening polysaccharide is gelated by temperature lowering in a temperature range from the second phase transition point to the first phase transition point. The aqueous solution of the thickening polysaccharide is obtained by solating a second aqueous dispersion liquid in which the thickening polysaccharide has been dispersed in water by temperature raising.

Specifically, a temperature at which the aqueous dispersion liquid in which the agar has been dissolved in water is solated when raising the temperature of the aqueous dispersion liquid of the agar in which 1.0% by mass of the agar (A) has been dispersed in water from room temperature is defined as the first phase transition point, and a temperature at which the aqueous solution is gelated when leaving the solated aqueous solution of the agar at room temperature to lower the temperature is defined as the second phase transition point. The thickening polysaccharide (B) is preferably thickening polysaccharide in which an aqueous dispersion liquid of 1.0% by mass of the thickening polysaccharide does not have a sol-to-gel phase transition point in the temperature range from the second phase transition point to the first phase transition point.

The aqueous dispersion liquid of 1.0% by mass of the thickening polysaccharide preferably does not have a sol-to-gel phase transition point in the temperature range of 10° C. to 95° C., more preferably does not have a sol-to-gel phase transition point in the temperature range of 5° C. to 99° C., and further preferably does not have a sol-to-gel phase transition point in the temperature range of 0° C. to 100° C.

The phrase "not having a sol-to-gel phase transition point in the temperature range" means that not having a sol-to-gel phase transition point when the temperature is raised from the lower limit of the above-mentioned temperature range, and when the temperature is lowered from the upper limit of the above-mentioned temperature range.

Regarding the notation of the concentrations of the aqueous dispersion liquid and the aqueous solution in the specification of the present application, 1.0% by mass is the concentration being from 0.95% by mass to 1.04% by mass by weighing in other words.

The inventors of the present invention think that when the thickening polysaccharide (B) does not have the above-mentioned phase transition point, this indicates that the thickening polysaccharide has flowability in the above-mentioned temperature range in the ultrasound phantom. That is, the thickening polysaccharide is preferably present in a sol state in the above-mentioned temperature range. It is thought that since the thickening polysaccharide is a sol (fluid) in the above-mentioned temperature range, the thickening polysaccharide having flowability is uniformly dispersed in the agar in the sol state by heating.

As the thickening polysaccharide, those in which the factor of gelation does not depend on the temperature change in the above-mentioned temperature range can be adopted. The thickening polysaccharide (B) is preferably water-soluble thickening polysaccharides. As the thickening polysaccharide, those to be described later may be used alone, or a plurality thereof may be used in a mixture. When a plurality of thickening polysaccharides are mixed and used, it is sufficient to select a combination in which this mixture does not have a sol-to-gel phase transition point in the above-mentioned temperature range.

From the studies by the inventors of the present invention, it was found that there are problems of ameliorating brittleness and preventing water separation when using the agar gel as the ultrasound phantom. It is presumed that the gel tissue constituting the agar phantom is destroyed by the repeated pressure when the ultrasound probe is pressed against the agar phantom.

It is thought that when the thickening polysaccharide does not have the above-mentioned phase transition point, the thickening polysaccharide (B) has flowability and exhibit stickiness in the hydrogel formed by the agar and the water in the ultrasound phantom, and thereby the brittleness can be ameliorated. Accordingly, the ultrasound phantom is less likely to break when the probe is pressed against it, which makes repeated use possible.

The thickening polysaccharide is not particularly limited as long as it does not have the above-mentioned phase transition point, and known thickening polysaccharides can be used. For example, the thickening polysaccharide indicates those in which an aldose monosaccharide typified by glucose, galactose, mannose, xylose, or the like, or a monosaccharide such as a derivative of an aldose monosaccharide such as glucuronic acid or deoxy sugar is bonded to a glycoside.

The thickening polysaccharide preferably has a side chain. The thickening polysaccharide is preferably a thickening polysaccharide to which at least one selected from the group consisting of a sugar chain selected from monosaccharides (such as aldose monosaccharides or derivatives thereof) and derivatives thereof and polysaccharides and derivatives thereof, a carboxymethyl group, a salt of a carboxymethyl group, a carboxy group, and a salt of a carboxy group is bonded as a side chain.

When the side chain is a polysaccharide, the polysaccharide as a side chain contains a saccharide that hydrolyzes to generate two or more molecules of monosaccharides.

Preferable examples of the thickening polysaccharide having the side chain include guar gum, diutan gum, xanthan gum, and cellulose derivatives. For example, a sodium salt of carboxymethyl cellulose is a cellulose derivative having a sodium salt of a carboxymethyl group at a side chain.

In addition, examples of the derivatives in the derivatives of monosaccharides and the derivatives of polysaccharides include derivatives in which hydroxyl groups of monosaccharides and polysaccharides have been substituted with at least one selected from the group consisting of a hydroxypropyl group, a hydroxypropyltrimonium chloride group, a carboxymethyl group, salts of a carboxymethyl group, a phosphate group, a hydroxyethyl group, a hydroxypropylmethyl group, and the like. They are preferably derivatives in which there is substitution with at least one selected from the group consisting of a hydroxypropyl group, a carboxymethyl group, and salts of a carboxymethyl group.

Examples of the salts include sodium salts, potassium salts, and ammonium salts, but sodium salts are preferable.

The polysaccharides having these side chains tend to a high 1.0% by mass viscosity value which is a value of the viscosity when 1.0% by mass thereof is dissolved in water. It is thought that this is because a sugar and a carboxy group in the side chain have a high affinity for water. Therefore, adding a small amount thereof can further ameliorate the brittleness of the ultrasound phantom. The 1.0% by mass viscosity value of the thickening polysaccharide is preferably from 100 mPa·s to 10,000 mPa·s. It is more preferably from 200 mPa·s to 9,000 mPa·s, and further preferably from 300 mPa·s to 8,000 mPa·s. The measurement of the 1.0% by mass viscosity value can be performed using a rotary viscometer. The viscosity in this case was measured using a parallel plate having the diameter of 25 mm, and using a dynamic viscoelasticity measurement device (MCR 302 sold by Anton Paar Japan K.K.). In addition, the rotation rate measured at this time was 5 (r/s).

Examples of the thickening polysaccharide include at least one selected from the group consisting of xanthan gum, tamarind seed gum, galactomannan (locust bean gum, tara gum, guar gum, and the like), succinoglycan, and diutan gum, and derivatives thereof, and cellulose derivatives. The thickening polysaccharide is preferably at least one selected from the group consisting of locust bean gum, tara gum, guar gum, xanthan gum, and diutan gum, and derivatives thereof, and cellulose derivatives, and more preferably at least one selected from the group consisting of guar gum, xanthan gum, and diutan gum, and derivatives thereof, and cellulose derivatives.

Similar to the above, examples of derivatives of these thickening polysaccharides include derivatives in which hydroxyl groups have been substituted with at least one selected from the group consisting of a hydroxypropyl group, a hydroxypropyltrimonium chloride group, a carboxymethyl group, salts of a carboxymethyl group, a phosphate group, a hydroxyethyl group, a hydroxypropylmethyl group, and the like. They are preferably derivatives in which there is substitution with at least one selected from the group consisting of a hydroxypropyl group, a carboxymethyl group, and salts of a carboxymethyl group. The derivative of guar gum is preferably hydroxypropyl guar.

When there is a derivative, the entanglement of the main chain of the thickening polysaccharide (B) is easily disentangled, which makes it possible to improve the solubility and obtain a uniform sol solution.

The cellulose derivative is preferably at least one selected from the group consisting of carboxymethyl cellulose, methyl cellulose, hydroxyethyl cellulose, hydroxypropyl cellulose, hydroxyethyl methyl cellulose, and hydroxypropylmethyl cellulose, and salts thereof. Examples of the salts include sodium salts, potassium salts, and ammonium salts, but sodium salts are preferable.

As for a side chain, in addition to those described above, one modified with a carboxy group for the main chain of the polysaccharide can also be used. For example, sodium carboxymethyl cellulose is more preferable.

The formulation amount or content of the thickening polysaccharide is preferably from 0.50 parts by mass to 2.00 parts by mass when a total mass of the water and the water-retention auxiliary agent is 100.00 parts by mass. When the thickening polysaccharide is 0.50 parts by mass or more, the brittleness of the phantom can be further ameliorated. Furthermore, by thickening the water contained in the ultrasound phantom, the sedimentation of each component can be prevented. When the thickening polysaccharide is 2.00 parts by mass or less, the viscosity is suitable, which makes the handling favorable. The formulation amount or content of the thickening polysaccharide is more preferably from 0.50 parts by mass to 1.00 parts by mass when a total mass of the water and the water-retention auxiliary agent is 100.00 parts by mass.

Water-Retention Auxiliary Agent (C)

The ultrasound phantom contains a water-retention auxiliary agent that is different from the agar and the thickening polysaccharide to delay the water separation of the hydrogel. The water-retention auxiliary agent indicates a compound having the action of preventing the evaporation of water. The water-retention auxiliary agent is preferably a water-soluble or water-miscible substance. As the water-retention auxiliary agent, one having a polar term $\delta P$ of 13.0 MPa$^{0.5}$ or more in Hansen solubility parameters (HSP) is used.

The Hansen solubility parameters can be calculated by computer software "Hansen Solubility Parameters in Practice (HSPiP)" and can be obtained using a known method. The Hansen solubility parameters in the present specification are values calculated by utilizing a version 5.3.05 of HSPiP.

The polar term $\delta P$ in the Hansen solubility parameters of the water-retention auxiliary agent (C) is preferably 14.0 MPa$^{0.5}$ or more, more preferably 16.0 MPa$^{0.5}$ or more, and further preferably 18.0 MPa$^{0.5}$ or more. The upper limit is not particularly limited, but it is preferably 30.0 MPa$^{0.5}$ or less, more preferably 25.0 MPa$^{0.5}$ or less, further preferably 22.0 MPa$^{0.5}$ or less, and further more preferably 20.0 MPa" or less. According to the studies by the inventors of the present invention, it was found that the polar term component $\delta P$ has a higher correlation coefficient with respect to a stable water retention rate than the other HSP components.

Compounds having the above-mentioned action may be collectively referred to as a chaotropic agent. The water-retention auxiliary agent preferably includes the chaotropic agent. The chaotropic agent has the action of changing the interaction between water molecules in the aqueous solution. By adding a compound having a polar term dP in the above-mentioned range as the water-retention auxiliary agent, the interaction of water molecules is changed, and thereby the water molecules can be strongly attracted. The degree of such interaction is represented by the polar term $\delta P$, and when a compound having this value in the above-mentioned range as the water-retention auxiliary agent (C) is used, this enables to embody stability over time as the phantom.

According to the studies by the inventors of the present invention, it was found that the phantom produced with the agar has a large change in water content. When water bleeds out of the phantom, the acoustic characteristics relating to ultrasound propagation change. Therefore, even when the phantom adjusted to match the acoustic characteristics of a human body is produced, characteristics changes are likely to occur over time, and only a numerical value of about that of an index is obtained. Even when the surface of the phantom is covered with a film or the like to prevent evaporation, it is difficult to reduce the bleeding out (water separation) of water from the phantom. When the water-retention auxiliary agent is used, the water-retention auxiliary agent strongly attracts water molecules, and thereby water separation is prevented, and the stability over time is improved.

The water-retention auxiliary agent (C) is not particularly limited as long as it satisfies the above-mentioned polar term $\delta P$. As the water-retention auxiliary agent, at least one selected from the group consisting of inositols such as myo-inositol, dimethyl sulfoxide (DMSO), urea, guanidine and guanidine salts, and derivatives thereof can be used, for example. Furthermore, as these derivatives, methylated, dimethylated, ethylated, and diethylated ones can also be used, for example. The water-retention auxiliary agent (C) preferably contains at least one selected from the group consisting of inositol, dimethyl sulfoxide, and urea.

The content of the water-retention auxiliary agent in the ultrasound phantom is preferably 1% by mass or more based on the total mass of the water and the water-retention auxiliary agent. Accordingly, a sufficient water retention effect can be obtained, which makes it possible to prevent bleeding out of water. The content of the water-retention auxiliary agent is preferably from 1.00% by mass to 15.00% by mass, more preferably from 2.00% by mass to 10.00% by mass, and further preferably from 4.00% by mass to 8.00% by mass based on the total mass of the water and the water-retention auxiliary agent.

In addition, since the water-retention auxiliary agent changes the interaction of water, the sound speed of ultrasound may change in some cases. Because the sound speed of organs of a biological body is about 1,535 (m/s), addition may be within the range that does not significantly deviate from this value. For example, the sound speed of ultrasound when ultrasound having the frequency of 3.5 MHz is transmitted through the ultrasound phantom is preferably from 1,525 m/s to 1,545 m/s, more preferably from 1,528 m/s to 1,540 m/s, and further preferably from 1,530 m/s to 1,537 m/s.

Other Component (D)

Various components can be added to the ultrasound phantom as needed as other components different from the agar, the thickening polysaccharide, and the water-retention auxiliary agent. For example, the ultrasound phantom may further contain an ultrasound scattering agent. In an ultrasound diagnostic apparatus, imaging and measurement are performed using a signal that has reached a detector among ultrasound scattered in the phantom. Therefore, by adding the ultrasound scattering agent to a portion to be measured, imaging becomes possible, which makes it possible to perform the measurement of the Young's modulus.

In addition, the scattering efficiency of ultrasound is calculated by the acoustic impedance (=density×sound speed) of the substance. At the material interface, the scattering efficiency increases as the difference in this value increases.

Examples of solid particles that can be used as the ultrasound scattering agent include known ones such as metals, metal oxides, carbon particles, and spherical polymers. The material of the ultrasound scattering agent is not particularly limited as long as it is a solid having low water solubility. From mechanical stability, particles of carbon crystals such as graphite and microdiamond, resin particles such as polyethylene particles, polyethylene hollow spheres, and polystyrene hollow spheres, fine particles of oxides such as titanium oxide, alumina oxide, and silicon oxide, fine particles of metals such as tungsten, nickel, and molybdenum, and the like are preferable. Among these, particles of carbon crystals are particularly preferable in consideration of the magnitude of acoustic impedance and the dispersibility in water.

The particle diameter of the ultrasound scattering agent is determined according to the wavelength of ultrasound input. The particle size of the ultrasound scattering agent is preferably from 5 μm to 50 μm when calculated from the wavelength of ultrasound emitted from a probe of an ultrasound diagnostic apparatus. It is more preferably from 5 μm to 25 μm.

However, particles having the particle diameter of 5 μm or more and having a high density generally have a high sedimentation velocity, and may be separated during the gelation of the agar from the sol. Such a sedimentation velocity can be calculated from the following Stokes equation.

$$V = g(\rho s - \rho 0)d^2/18\eta$$

(V: sedimentation velocity, g: gravitational acceleration, ρs: particle density, ρ0: solvent density, d: particle diameter, η viscosity rate of solvent)

The value of η in Stokes equation increases by adding the thickening polysaccharide (B), which makes it possible to delay the sedimentation of the ultrasound scattering agent.

The content of the ultrasound scattering agent may be appropriately adjusted according to the target scattering effect, and is not particularly limited, but it is preferably from 0.50 parts by mass to 20.00 parts by mass, more preferably from 1.00 parts by mass to 10.00 parts by mass, and further preferably from 2.00 parts by mass to 7.00 parts by mass when the total mass of the water and the water-retention auxiliary agent is 100.00 parts by mass.

Furthermore, the ultrasound phantom may contain a preservative as the other components. In general, hydrogels are prone to mold generation, and when used for calibration, it is preferable to use a preservative to prevent the influence on physical property values. The preservative that can be used is not particularly limited, but a preservative that is water-soluble and has a wide antimicrobial spectrum is preferable.

Examples of preservatives, fungicides, or antimicrobial agents as a compound that can prevent mold growth include alkyl diaminoethyl glycine hydrochloride, sodium benzoate, ethanol, benzalkonium chloride, benzethonium chloride, chlorhexidine gluconate, chlorobutanol, sorbic acid, potassium sorbate, sodium dehydroacetate, methyl paraoxybenzoate, ethyl paraoxybenzoate, propyl paraoxybenzoate, butyl paraoxybenzoate, oxyquinoline sulfate, phenethyl alcohol, and benzyl alcohol.

Among these, the paraoxybenzoate ester type is desirable because it is water-soluble, has a wide antimicrobial spectrum, and is particularly desirable to have little influence on a human body. Furthermore, methyl paraoxybenzoate is particularly preferable from the viewpoint of water solubility.

Because the effect of the preservative differs depending on each compound, it is preferable to add it as appropriate. For example, in the case of methyl paraoxybenzoate, 0.20 parts by mass to 0.30 parts by mass may be added, and 0.25 parts by mass, which is the saturation amount, is preferably added when the total mass of the water and the water-retention auxiliary agent is 100.00 parts by mass. Accordingly, the effect as the preservative becomes sufficient.

A method for manufacturing the ultrasound phantom is not particularly limited. Water, the agar, the thickening polysaccharide, and the water-retention auxiliary agents, and, as necessary, the other components such as the ultrasound scattering agent and the preservative are mixed. In addition, the temperature of the mixture is raised to a temperature exceeding the first phase transition point (for example, from 85° C. to 99° C.) at which the agar dissolves in water to dissolve the agar in water, thereby obtaining a dissolved solution. As necessary, stirring or heating is performed until the distribution of the contained components in the solution becomes uniform. The distribution of the contained components in the solution includes an aspect of reaching equilibrium in a state where they are macroscopically and uniformly dispersed in the solvent, and an aspect of reaching equilibrium in which they are microscopically and uniformly dissolved in the solvent at the molecular level. The former contains the ultrasound scattering agent and the preservative, and the latter contains the agar, the thickening polysaccharide, and the water-retention auxiliary agent. The ultrasound phantom can be obtained by pouring the obtained mixed solution into a mold having a desired shape, and cooling to a temperature below the second phase transition point at which the agar is gelated.

That is, the method for manufacturing the ultrasound phantom preferably includes cooling the mixed solution, which contains the water, the agar, the thickening polysaccharide, and the water-retention auxiliary agent and which is in the state where the agar is dissolved in the water, to the temperature at which the agar is gelated to obtain the ultrasound phantom. This makes it possible to obtain the ultrasound phantom containing the hydrogel containing the water, the agar, the thickening polysaccharide, and the water-retention auxiliary agent.

In addition, the method for manufacturing the ultrasound phantom preferably has the following steps:

a step of raising the temperature of the mixture in which water and the agar (and the preservative as necessary) are mixed to the temperature (first phase transition point) at which the agar dissolves in water to obtain a liquid A in which the agar has dissolved in water;

a step of mixing the thickening polysaccharide (and the ultrasound scattering agent as necessary) to an aqueous solution of the water-retention auxiliary agent obtained by mixing water and the water-retention auxiliary agent to obtain a liquid B; and a step of mixing the obtained liquid A and liquid B, and cooling the obtained mixed solution to obtain the ultrasound phantom.

Any of the step of obtaining the liquid A and the step of obtaining the liquid B may be performed first, or both may be performed at the same time. The temperature may be raised after mixing the liquid B. The temperature of the liquid B may be raised to such an extent that the temperature difference between the liquid A and the liquid B is small, and it is preferable to perform heating to a temperature of about the first phase transition point (for example, from 85° C. to 99° C.). Regarding the liquid A and the liquid B, it is preferable that the mixed solution be homogenized in a container. The mixing is preferably performed while maintaining the temperature from 85° C. to 99° C.

The obtained mixed solution is poured into a mold having a desired shape as needed, and cooled to a temperature below the second phase transition point (for example, room temperature) to gelate the agar, thereby obtaining the ultrasound phantom. A cooling method is not particularly limited, and the mold may be left at room temperature, or may be cooled using a desired medium such as water.

The Young's modulus E of the ultrasound phantom measured by a viscoelasticity measurement device is preferably from 50 kPa to 2,000 kPa, more preferably from 100 kPa to 1,500 kPa, and further preferably from 120 kPa to 1,000 kPa. The hardness can be adjusted by adjusting the concentration of the agar, and the like. The ultrasound phantom can have a constant sound speed close to the sound speed in a biological body without depending on the hardness.

The ultrasound phantom can be used for the calibration of a device as a phantom for ultrasound inspection in ultrasound diagnostic apparatuses such as ultrasound elastography for calculating an accurate Young's modulus of an organ, for example.

EXAMPLES

Hereinafter, the present invention will be described in detail with reference to examples, but the present invention is not limited to these examples. In the following formulations, parts are mass-based unless otherwise noted.

Material

The materials used in examples and comparative examples are listed below.

Gelling Agent (A)

A-1: Agar; "Agar, powder (KISHIDA CHEMICAL CO., LTD.)"

Thickening Polysaccharide (B)

B-1: Hydroxypropyl guar; "ESAFLOR 4W (Sansho Co., Ltd.)"

B-2: Xanthan gum; "Kelzan® AP (Sansho Co., Ltd.)"

B-3: Diutan gum; "Kelco-Vis DG (Sansho Co., Ltd.)"

B-4: Carboxy group-modified cellulose; "CEKOL 30000 (Sansho Co., Ltd.)"

These are thickening polysaccharides not having a sol-to-gel phase transition point in the temperature range described above.

Water-Retention Auxiliary Agent (C)

C-1: Urea (KISHIDA CHEMICAL CO., LTD.)

C-2: Dimethyl sulfoxide (DMSO) (Tokyo Chemical Industry Co., Ltd.)

C-3: Myo-inositol (Tokyo Chemical Industry Co., Ltd.)

C-4: Glycerin (KISHIDA CHEMICAL CO., LTD.)

C-5: Mannitol (Tokyo Chemical Industry Co., Ltd.)

Other Component (D)

D-1: Graphite; "NICABEADS® ICB 1020 (Nippon Carbon Co., Ltd.)"

D-2: Methyl paraoxybenzoate (KISHIDA CHEMICAL CO., LTD.)

Evaluation Method

Water Separation Rate

The ultrasound phantom was stored in an airtight container having a constant space, and the water separation rate was evaluated by measuring the rate of decrease in mass due to evaporation of water or bleeding out of water after 24 days. The ultrasound phantom having the diameter of 30 mm and the thickness of 5 mm was put in the space of about 30 cm³ and stored in a refrigerator (about 4° C.) for 24 days. By comparing to a reference example in which the water-retention auxiliary agent was not added, one in which the water separation rate decreased was denoted by 0, and one in which the water retention rate increased was denoted by X.

Brittleness

When a probe is manually pressed against the ultrasound phantom, a large force is unintentionally applied, which may damage the ultrasound phantom. The brittleness of the ultrasound phantom was verified by assuming the pressing movement of the probe as the compression when pressing a jig.

A compression test was performed using a universal tester (RTF-1250, manufactured by A&D Company, Limited). An ultrasound phantom having the diameter of 30 mm and the thickness of 50 mm was produced and compressed under the condition of 2 mm/min.

Japanese Patent No. 5787286 discloses the relationship between the force and the deformation of an organ when an ultrasound probe is pressed against a biological body. In an elastography in an ultrasound diagnostic apparatus, it is rare to press an organ strongly to quantitatively determine the Young's modulus of the organ itself, but it is assumed that the force from 500 gf to 1,000 gf is applied.

In the brittleness test, in the compression test, an S-S curve was drawn, and one in which an inflection point or yield point was observed at the compressive stress of 30 kPa or less was regarded as internal collapse. One with the internal collapse was denoted by X, and one without it was denoted by O.

Young's Modulus

The measurement was performed using a viscoelasticity measurement device (MCR 302 sold by Anton Paar Japan K.K.) to obtain the value of a storage elastic modulus G'. The measurement of the storage elastic modulus was performed using a cylindrical ultrasound phantom produced to have the diameter of 30 mm and the thickness of 5 mm. The storage elastic modulus G' was measured by contacting and vibrating a parallel plate having the diameter of 25 mm from the upper part of the ultrasound phantom.

The Young's modulus E of the ultrasound phantom was calculated from the storage elastic modulus G' using a Poisson's ratio v by the following equation.

$$E = G' \cdot 2(1+v)$$

Since the volume change of the ultrasound phantom at the time of measurement was small, it can be assumed that the Poisson's ratio v=0.5. Based on this, E=3·G', and by tripling the value of the storage elastic modulus G', the value of the Young's modulus E was obtained.

Sound Speed

The measurement of the sound speed was performed by measuring the transmission time of ultrasound to the ultrasound phantom. Using a jig, the ultrasound phantom was fixed in water between a transducer with the measurement frequency of 3.5 MHz (V328-SU manufactured by Olympus Corporation) and a needle-type hydrophone (manufactured by Toray Engineering D Solutions Co., Ltd.) such that the incidence angle of an ultrasound signal was 0°.

In a state where test pieces of two types of ultrasound phantom having the length 100 mm×width 100 mm and the thicknesses of 5 mm and 10 mm were installed as described above, a three-cycle sine wave generated by a waveform generator was oscillated from an ultrasound oscillator, and the waveform data received with an ultrasound geophone was measured with an oscilloscope.

For the value of the sound speed, the average value of the values at the thicknesses of 5 mm and 10 mm was used.

Method of Producing Ultrasound Phantom

Manufacturing Example

The production procedure of Example 1 is described as an example of the manufacturing procedure of the ultrasound phantom. In the other examples and the manufacturing example, without changing this procedure, phantoms were produced by changing only the type and amount of the material according to the formulations shown in Tables 1, 2, and 3. The phantoms were produced using separate formulations for an adjustment liquid A for adjusting the gelling agent and an adjustment liquid B for adjusting the water-retention auxiliary agent, and mixing them.

Adjustment Liquid A 250 g (50.00 parts) of ion exchange water, 14.4 g (2.88 parts) of agar, and 1.25 g (0.25 parts) of methyl paraoxybenzoate were put in an airtight container, and heated in a heating oven at 90° C. for 4 hours.

Adjustment Liquid B 220 g (44.00 parts) of ion exchange water and 30 g (6.00 parts) of urea were dissolved in an airtight container to prepare a 12% urea aqueous solution. 3.75 g (0.75 parts) of hydroxypropyl guar was added thereto and dissolved. 20 g (4.00 parts) of graphite was further added thereto. The mixture was sufficiently stirred, and thereafter heated in a heating oven at 90° C. for 1 hour.

In the state of heating the adjustment liquid A and the adjustment liquid B at 90° C., mixing was performed according to the ratio of each of the constituent components such that the amount of the ion exchange water in the adjustment liquid A and the amount of urea water in the adjustment liquid B were equal to each other. After stirring treatment for 2 minutes, the mixture was poured into a mold and cooled to obtain an ultrasound phantom.

TABLE 1

| | | | | | | Comparative | Comparative | Reference |
|---|---|---|---|---|---|---|---|---|
| | | | Example 1 | Example 2 | Example 3 | Example 1 | Example 2 | Example |
| Material | Ion exchange water | | 94 | 94 | 94 | 94 | 94 | 94 |
| | Agar (A) | A-1 | 2.88 | 2.88 | 2.88 | 2.88 | 2.88 | 2.88 |
| | Thickening polysaccharide (B) | B-1 | 0.75 | 0.75 | 0.75 | 0.75 | 0.75 | 0.75 |
| | Water-retention auxiliary agent (C) | C-1 | 6 | | | | | |
| | | C-2 | | 6 | | | | |
| | | C-3 | | | 6 | | | |
| | | C-4 | | | | 6 | | |
| | | C-5 | | | | | 6 | |
| | Other component (D) | D-1 | 4 | 4 | 4 | 4 | 4 | 4 |
| | | D-2 | 0.25 | 0.25 | 0.25 | 0.25 | 0.25 | 0.25 |
| Evaluation | δP value of component C | | 19.8 | 14.6 | 13.0 | 12.7 | 11.2 | — |
| | Water separation rate test | | ○ (5.8%) | ○ (7.0%) | ○ (15.3%) | x (32.8%) | x (21.4%) | (19.2%) |

<p style="text-align:center">Result of water separation rate test</p>

In Tables 1, 2, and 3, the numerical value of each material indicates the number of parts.

Table 1 shows the results of performing the above-mentioned water separation rate test. In the reference example in which the water-retention auxiliary agent was not added, 19.2% by mass of water was separated in 24 days. Meanwhile, Comparative Example 1 and Comparative Example 2 are examples in which a polyhydric alcohol generally used for adjusting the sound speed was added. The δP values (MPa$^{0.5}$) of glycerin (Comparative Example 1) and mannitol (Comparative Example 2) were 12.7 and 11.2, respectively, and both were 13.0 or less. In this case, the result in which the water separation rate was higher than the value in the reference example was obtained. On the other hand, in the cases of Example 1, Example 2, and Example 3 in which the value of δP of the water-retention auxiliary agent was larger than 13.0, the water separation rate was significantly ameliorated as compared to the reference example.

TABLE 2

| | | | | | | | Comparative |
|---|---|---|---|---|---|---|---|
| | | | Example 4 | Example 5 | Example 6 | Example 7 | Example 3 |
| Material | Ion exchange water | | 94 | 94 | 94 | 94 | 94 |
| | Agar (A) | A-1 | 2.88 | 2.88 | 2.88 | 2.88 | 2.88 |
| | Thickening polysaccharide (B) | B-1 | 0.75 | | | | |
| | | B-2 | | 0.75 | | | |
| | | B-3 | | | 0.75 | | |
| | | B-4 | | | | 0.75 | |

<p style="text-align:center">Brittleness test</p>

TABLE 2-continued

| | | | Brittleness test | | | |
|---|---|---|---|---|---|---|
| | | | Example 4 | Example 5 | Example 6 | Example 7 | Comparative Example 3 |
| | Water-retention auxiliary agent (C) | C-1 | 6 | 6 | 6 | 6 | 6 |
| | Other component (D) | D-1 | 4 | 4 | 4 | 4 | 4 |
| | | D-2 | 0.25 | 0.25 | 0.25 | 0.25 | 0.25 |
| Evaluation | Compression test | | ○ | ○ | ○ | ○ | x |

In Comparative Example 3 in which the thickening polysaccharide was not added, internal collapse was observed at 30 kPa or less. On the other hand, in Examples 4 to 7 in which the thickening polysaccharide were added, internal collapse was not observed, and the ultrasound phantom with ameliorated brittleness was obtained.

TABLE 3

| | | | Young's modulus test | | | | | | |
|---|---|---|---|---|---|---|---|---|---|
| | | | Example 8 | Example 9 | Example 10 | Example 11 | Example 12 | Example 13 | Example 14 |
| Material | Ion exchange water | | 94 | 94 | 94 | 94 | 94 | 94 | 94 |
| | Agar (A) | A-1 | 1.72 | 2.30 | 2.80 | 3.17 | 4.62 | 5.55 | 5.78 |
| | Thickening polysaccharide (B) | B-1 | 0.625 | 0.625 | 0.625 | 0.625 | 0.625 | 0.625 | 0.625 |
| | Water-retention auxiliary agent (C) | C-1 | 6 | 6 | 6 | 6 | 6 | 6 | 6 |
| | Other component (D) | D-1 | 4 | 4 | 4 | 4 | 4 | 4 | 4 |
| | | D-2 | 0.25 | 0.25 | 0.25 | 0.25 | 0.25 | 0.25 | 0.25 |
| Evaluation | Water separation rate test | | ○ | ○ | ○ | ○ | ○ | ○ | ○ |
| | Compression test | | ○ | ○ | ○ | ○ | ○ | ○ | ○ |
| | Young's modulus (kPa) | | 133 | 227 | 346 | 403 | 612 | 773 | 959 |
| | Sound speed (m/s) | | 1533 | 1530 | 1532 | 1534 | 1535 | 1530 | 1534 |

Examples 8 to 14 are ultrasound phantoms obtained by preparing a calibration curve relating to the Young's modulus to adjust the concentration of the agar (A). The water separation and brittleness were ameliorated in all of the ultrasound phantoms. Furthermore, all of the examples had the value of the sound speed close to the sound speed of a biological body (1,535 (m/s)), and can be suitably used for the calibration of an ultrasound diagnostic apparatus.

As described above, according to the present disclosure, the phantom in which the problems of the conventional agar phantoms have been greatly ameliorated could be obtained.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-161704, filed Sep. 30, 2021, which is hereby incorporated by reference herein in its entirety.

What is claimed is:

1. An ultrasound phantom, comprising:
water;
agar configured to form a hydrogel with at least part of the water;
a thickening polysaccharide dispersed in the hydrogel and configured to thicken the hydro gel; and
a water-retention auxiliary agent dispersed in the hydrogel and configured to reduce a water separation from the hydrogel, wherein a content of the agar is 0.25 to 20.00 parts by mass when a total mass of the water and the water-retention auxiliary agent is 100.00 parts by mass,
a content of the thickening polysaccharide is 0.50 to 2.00 parts by mass when a total mass of the water and the water-retention auxiliary agent is 100.00 parts by mass,
a content of the water-retention auxiliary agent is 1.00 to 15.00% by mass based on a total mass of the water and the water-retention auxiliary agent,
when a first phase transition point is defined as a temperature at which an aqueous dispersion liquid of the agar is solated by temperature raising and becomes a solated aqueous solution of the agar, and a second phase transition point is defined as a temperature at which the solated aqueous solution of the agar is gelated by temperature lowering, the thickening polysaccharide has flowability as a sol in a temperature range from the second phase transition point to the first phase transition point and does not have a phase transition point at which an aqueous solution of the thickening polysaccharide is gelated by temperature lowering in the temperature range, and
a polar term $\delta P$ of Hansen solubility parameters of the water-retention auxiliary agent is 13.0 MPa$^{0.5}$ or more.

2. The ultrasound phantom according to claim 1, wherein the first phase transition point of the agar is present at 85 to 99° C., and
the second phase transition point of the agar is present at 30 to 45° C.

3. The ultrasound phantom according to claim 1, wherein the aqueous dispersion liquid of the agar is obtained by dispersing the agar in water, and
the aqueous solution of the thickening polysaccharide is obtained by solating a second aqueous dispersion liquid in which the thickening polysaccharide is dispersed in water by temperature raising.

4. The ultrasound phantom according to claim 3, wherein the first phase transition point is the temperature at which the aqueous dispersion liquid of the agar is solated when raising the temperature of the aqueous dispersion liquid of the agar, and the second phase transition point is the temperature at which the solated aqueous solution of the agar is gelated when lowering the temperature thereof.

5. The ultrasound phantom according to claim 1, wherein the aqueous solution of the thickening polysaccharide does not have a sol-to-gel phase transition point in the temperature range.

6. The ultrasound phantom according to claim 1, wherein the water-retention auxiliary agent comprises a chaotropic agent.

7. The ultrasound phantom according to claim 1, wherein the water-retention auxiliary agent comprises at least one of inositol, dimethyl sulfoxide or urea.

8. The ultrasound phantom according to claim 1, wherein at least one member selected from the group consisting of a sugar chain selected from monosaccharides and derivatives thereof and polysaccharides and derivatives thereof, a carboxymethyl group, a salt of a carboxymethyl group, a carboxy group, and a salt of a carboxy group is bonded as a side chain to the thickening polysaccharide.

9. The ultrasound phantom according to claim 1, wherein the thickening polysaccharide comprises at least one member selected from the group consisting of xanthan gum, tamarind seed gum, galactomannan, succinoglycan, diutan gum, and derivatives thereof, and cellulose derivatives.

10. The ultrasound phantom according to claim 1, wherein the thickening polysaccharide comprises at least one member selected from the group consisting of guar gum, xanthan gum and diutan gum, and derivatives thereof, and cellulose derivatives.

11. The ultrasound phantom according to claim 1, further comprising an ultrasound scattering agent.

12. The ultrasound phantom according to claim 1, further comprising a preservative.

13. A method for manufacturing the ultrasound phantom according to claim 1, the method comprising:

cooling a mixed solution comprising the water, the agar, the thickening polysaccharide and the water-retention auxiliary agent, and which is in a state where the agar is dissolved in the water, to a temperature at which the agar is gelated to obtain the ultrasound phantom.

14. The ultrasound phantom according to claim 1, wherein the thickening polysaccharide does not have a sol-to-gel phase transition point in the temperature range of 10° C. to 95° C.

* * * * *